United States Patent [19]

Rong

[11] Patent Number: 5,654,460

[45] Date of Patent: Aug. 5, 1997

[54] METHOD FOR PRODUCTION OF AKLYLHALOSILANES

[75] Inventor: Harry Morten Rong, Kristiansand, Norway

[73] Assignee: Elkem a/s, Norway

[21] Appl. No.: 455,129

[22] Filed: May 31, 1995

[30] Foreign Application Priority Data

Feb. 28, 1995 [NO] Norway ................................. 950760

[51] Int. Cl.⁶ .............................. C07F 7/08; C07F 7/16
[52] U.S. Cl. .................................................. 556/472
[58] Field of Search ..................................... 556/472

[56] References Cited

U.S. PATENT DOCUMENTS

| | | | |
|---|---|---|---|
| 2,380,995 | 8/1945 | Rochow | 556/472 |
| 2,427,605 | 9/1947 | Hurd. | |
| 4,602,101 | 7/1986 | Halm et al.. | |
| 4,762,940 | 8/1988 | Halm et al.. | |
| 4,864,044 | 9/1989 | Lewis et al.. | |
| 4,946,978 | 8/1990 | Halm et al.. | |
| 5,068,385 | 11/1991 | Degen et al. | 556/472 |
| 5,362,897 | 11/1994 | Harada et al. | 556/472 |
| 5,380,903 | 1/1995 | Degen et al. | 556/472 |

FOREIGN PATENT DOCUMENTS

| | | |
|---|---|---|
| 0194214 | 10/1986 | European Pat. Off.. |
| 3425424 | 5/1988 | Germany. |
| 169831 | 11/1989 | Norway. |
| 2153697 | 8/1985 | United Kingdom. |

*Primary Examiner*—Paul F. Shaver
*Attorney, Agent, or Firm*—Lucas & Just

[57] ABSTRACT

The present invention relates to a method for production of alkylhalosilanes by reaction between elemental silicon and an alkylhalide at elevated temperatures in the presence of a copper-based catalyst and optionally promotors. Aluminium in the form of metallic aluminium, or an aluminium alloy, or an aluminium containing silicon alloy or an aluminium containing compound or mixtures thereof are added to the reactor in an amount between 0.01 and 1% by weight calculated as aluminium based on the weight of silicon supplied to the reactor.

8 Claims, No Drawings

METHOD FOR PRODUCTION OF AKLYLHALOSILANES

The present invention relates to a method for production of alkylhalosilanes.

It was well known prior to the present invention that alkylhalosilanes could be prepared by the direct reaction of alkylhalides with elemental silicon in the presence of a copper catalyst, for example as disclosed in U.S. Pat. No. 2,380,995. In practice, this reaction is carried out in a fluidized bed reactor or in a stirred bed reactor. Generally the reaction is carried out by passing the alkylhalide in vaporous form over the surface of the powdered silicon while maintaining the reaction mixture at an elevated temperature. Typically the elemental silicon is mixed with finally divided copper powder as described in U.S. Pat. No. 2,380,995, the copper serving as a catalyst for the reaction between the alkylhalide and the silicon.

In the production of organohalosilanes by the direct process the two primary reaction products are alkyltrihalosilane (T) and dialkyldihalosilane (D). The preferred product is dialkyldihalosilane and it is therefore normally a wish to produce a highest possible amount of dialkyldihalosilane and a low amount of alkyltrihalosilane. The ratio of alkyltrihalosilane to dialkyldihalosilane (T/D) is referred to as selectivity. The reaction between alkylhalide and silicon in the direct process also produces other by-products such as tetraalkylsilane, tetrahalosilane, polysilanes (referred to as "high Boilers") and hydrogen containing monomeric silanes. The production of these by-products should be minimized.

Another important feature of the direct process is the reactivity in the present application defined as grams of products/grams of silicon per hour. A high reactivity or reaction rate is vital for the productivity of a reactor.

The copper in the catalyst can for instance be in elemental form, in oxide form or in the form of copper chloride. A catalyst containing a mixture of different forms of copper can also be used. A number of additives can be used to promote the reactions, the most important being zinc, tin and antimony.

Also the composition and the structure of the silicon used in the direct process can be modified in order to improve reactivity and/or selectivity. Thus in Norwegian patent No. 169831 it is proposed to provide a silicon for use in the production of chlorosilanes and organochlorosilanes where the main impurities in silicon, Fe, Al and Ca, are in the form of the intermetallic phases $FeAl_3Si_2$ and/or $Fe_4Si_6Al_4Ca$. According to the Norwegian patent the ternary phase $FeAl_3Si_2$ gives an improved reactivity while the quaternary phase $Fe_4Si_6Al_4Ca$ gives an improved selectivity. It is further disclosed that a silicon product containing one or both of the above intermetallic phases is mixed with metallurgical grade silicon and where this mixture is used as a silicon source in the direct process.

As shown in Norwegian patent No. 169831 the reactivity is increased when $FeAl_3Si_2$ is present and the selectivity is improved when $Fe_4Si_6Al_4Ca$ is present. It has, however, been found that it is not possible to obtain an increase in both reactivity and selectivity when using the product and the process according to the Norwegian patent. Further it is difficult to obtain the specific intermetallic phases during solidification of molten silicon.

In GB-A 2153697 it is proposed to increase the reactivity and selectivity of the direct process by providing a copper catalyst consisting of a mixture of elemental copper, $Cu_2O$ and CuO, 200 to 5000 ppm tin-containing compound as tin relative to copper and from 50 to 5000 ppm aluminium or aluminium-containing compound as aluminium relative to copper. However, no significant increase in reactivity or selectivity is obtained by using the catalyst system of GB-A 2153697. Further when using a catalyst with a fixed aluminium content it is not possible to adjust the aluminium content in the reactor during the direct process as the catalyst has to be supplied to the reactor in an amount necessary to maintain a desired content of copper catalyst and not to independently regulate the aluminium content. Finally, mixtures of aluminium and copper oxides can result in a very strong exothermic reaction which may result in explosions.

It is an object of the present invention to provide a method for production of alkylhalosilanes by reaction between elemental silicon and an alkylhalide in the presence of a copper-based catalyst, wherein both reactivity and selectivity are improved over the prior art methods, and where the disadvantages of GB-A 2153697 are overcome.

Accordingly the present invention relates to a method for production of alkylhalosilanes by reaction between elemental silicon and an alkylhalide at elevated temperatures in the presence of a copper-based catalyst and optionally promotors, characterized in that aluminium in the form of metallic aluminium, or an aluminium alloy, or an aluminium containing silicon alloy, or an aluminium containing compound or mixtures thereof are added to the reactor in an amount between 0.01 and 1% by weight calculated as aluminium based on the weight of silicon supplied to the reactor.

The aluminium or the aluminium alloy or the aluminium containing silicon alloy or the aluminium containing compound or mixtures thereof are preferably added to the reactor separate from the silicon and the catalyst, but can also be mixed with the silicon or the catalyst prior to the addition to the reactor.

According to a preferred embodiment the aluminium, in the form of metallic aluminium or aluminium alloy or aluminium containing silicon alloy or aluminium containing compound or mixtures thereof is added to the reactor in an amount between 0.05 and 0.20% by weight calculated as aluminium based on the weight of silicon supplied to the reactor.

Aluminium can be added in the form of metallic aluminium and in the form of aluminium alloys such as alloys with Si, Cu, Fe, Mg, Zn and Ca. If an aluminium containing silicon alloy is used, such alloys contains at least 0.5% by weight of Al. In addition such alloys may contain iron, copper and calcium. As aluminium containing compounds solid, liquid and gaseous compounds can be used, such as for example aluminium halides, aluminium salts, such as aluminium carbonate, aluminium phosphate, aluminium sulphate and the like, other aluminium containing compounds such as aluminium hydroxide, aluminium sulphide and the like, and aluminium containing organic compounds, such as aluminium acetates aluminium oxalate, trialkoxyaluminium and the like.

Tests have shown that different Al containing sources give optimal results for different kinds of copper-catalyst used. Thus when a copper oxide-based catalyst is used it is preferred to add aluminium that reacts quickly with alkylhalide such as metallic aluminium or AlSi alloy to the reactor. On the other hand, when an elemental copper-based catalyst is used, it is also preferred to add aluminium in the form of Al-Fe-Si alloy to the reactor in addition to Al and AlSi alloys.

The method according to the present invention is particularly suited when silicon having a high amount of quaternary phase ($Al_6CaFe_4Si_8$) (a high Ca/Al ratio) is used as a source for elemental silicon.

By the present invention where aluminium, an aluminium containing alloy an aluminium containing silicon alloy or an aluminium containing compound or mixtures thereof are separately added to the reactor, it is possible to regulate the reactivity during the process by regulating the amount of Al source added to the reactor and thus prevent formation of hot spots in the reactor. Further it is possible to improve the operation of a reactor running at bad operation conditions without adding additional catalyst. Another advantage of the present invention is that one can adjust the total aluminium content in the reactor to a level which gives the best operation conditions for a certain reactor, taking into account varying amounts of aluminium in the silicon used in the process. The addition of aluminium according to the present invention further makes it possible to strongly increase the reactivity of silicon for low reactivity silicon products where the content of aluminium is difficult or impossible to control during the production of silicon.

It is believed that at the start of the reaction, active Al in the contact mass forms $Al_2Cl_6$ (g) which reacts with the native silicon dioxide layer on the silicon particles by formation of porous AlOCl. Thus the level of active Al in the charge is reduced shortly after start of the reaction. If silicon having a low content of active Al is thereafter added to the reactor, the reactor will run at a low reactivity which again results in reduced selectivity. By adding active aluminium in accordance with the present invention, active Al will always be present and will destroy native silicon dioxide layer on silicon particles added to the reactor during the process.

The present invention will now be further described by way of examples.

EXAMPLE 1

(Prior Art)

The tests were carried out in a stirred bed reactor with a diameter of 40 mm and equipped with a spiral stirrer. For each run 200 grams of silicon was charged to the reactor. The silicon was screened to a size of 71 to 250 μm. The reaction was catalysed with 10 grams of metallic copper, and promoted with antimony. Methyl chloride was supplied to the bottom of the reactor and kept at a constant flow rate of 65 standard liters/hour. The reactor was heated to 345° C. within 30 minutes and kept at this temperature throughout the run.

The silicon used in this experiment was Silgrain® silicon produced by Elkem a/s with a chemical composition of 0.27 wt. % Al, 0.39 wt. % Fe, 0.060 wt. % Ca, 0.024wt. % Ti. The duration of the run was 288 minutes at when about 5% of the silicon was converted. The reactivity was calculated as the average from the start of the reaction to the reactor was turned off. The selectivity is given as an average value of the stable period typically neglecting the first 60 minutes of the run. The results are given in Table 1

EXAMPLE 2

(Present Invention)

The reaction was repeated in the same manner as in Example 1, except that 1 gram of an aluminium promoter consisting of gas atomised 70% Al30% Si alloy was added separately to the contact mass of silicon and catalyst. The duration of the run was 374 minutes at when about 24% of the silicon was converted. The results are given in Table 1

TABLE 1

|  | Example 1 | Example 2 |
|---|---|---|
| Reactivity (gr. products/gr. Si * hr) | 0.05 | 0.21 |
| Selectivity [T/D] | 0.38 | 0.22 |
| $(CH_3)_2SiCl_2$[D] | 64.1 wt. % | 72.4 wt. % |
| $CH_3SiCl_3$ [T] | 24.6 wt. % | 16.0 wt. % |
| $(CH_3)_3SiCl$ [M] | 3.5 wt. % | 5.9 wt. % |
| $CH_3HSiCl_2$ + $(CH_3)_2HSiCl$ | 5.2 wt. % | 3.4 wt. % |
| High Boilers | 2.7 wt. % | 1.3 wt. % |

The results in Table 1 show that both the reactivity and the selectivity were strongly increased when adding the aluminium silicon alloy to the reactor.

EXAMPLE 3

(Prior Art)

The reaction was repeated in the same manner as in Example 1, except that the reaction was catalysed with 8 grams of copper(II)oxide (CuO) and promoted with zinc and tin added as 1.2 grams of ZnO and 0.024 grams of $SnO_2$. The silicon used in this experiment was Silgrain® silicon with a chemical composition of 0.25 wt. % Al, 0.24 wt. % Fe, 0.031 wt. % Ca, 0.013wt. % Ti. The duration of the run was 397 minutes at when about 18% of the silicon was converted. The results are given in Table 2.

EXAMPLE 4

(Present Invention)

The reaction was repeated in the same manner as in Example 3, except that 1 gram of an aluminium promoter consisting of gas atomised 70% Al30% Si alloy was added to the contact mass. The duration of the run was 281 minutes at when about 26% of the silicon was converted. The results are given in Table 2.

TABLE 2

|  | Example 3 | Example 4 |
|---|---|---|
| Reactivity (gr. products/gr. Si * hr) | 0.13 | 0.30 |
| Selectivity [T/D] | 0.10 | 0.04 |
| $(CH_3)_2SiCl_2$ [D] | 82.0 wt. % | 91.2 wt. % |
| $CH_3SiCl_3$ [T] | 8.2 wt. % | 3.9 wt. % |
| $(CH_3)_3SiCl$ [M] | 3.3 wt. % | 2.4 wt. % |
| $CH_3HSiCl_2$ + $(CH_3)_2HSiCl$ | 3.1 wt. % | 0.9 wt. % |
| High Boilers | 3.3 wt. % | 1.7 wt. % |

Also the results in Table 2 show a strongly increased reactivity and selectivity when using the method of the present invention.

EXAMPLE 5

(Prior Art)

The reaction was repeated in the same manner as in Example 3, except that a Silgrain® silicon sample with a chemical composition of 0.22 wt. % Al, 0.22 wt. % Fe, 0.028 wt. % Ca, 0.012 wt. % Ti was used. The duration of the run was 360 minutes at when about 14% of the silicon was converted. The results are given in Table 3.

EXAMPLE 6

(Present Invention)

The reaction was repeated in the same manner as in Example 5, except that 0.7 gram of an aluminium promoter consisting of gas atomised 85% Al15% Cu alloy was added to the contact mass. The duration of the run was 344 minutes at when about 32% of the silicon was converted. The results are given in Table 3.

TABLE 3

|  | Example 5 | Example 6 |
|---|---|---|
| Reactivity (gr. products/gr. Si * hr) | 0.11 | 0.32 |
| Selectivity [T/D] | 0.09 | 0.07 |
| $(CH_3)_2SiCl_2$ [D] | 83.8 wt. % | 87.0 wt. % |
| $CH_3SiCl_3$ [T] | 7.6 wt. % | 6.1 wt. % |
| $(CH_3)_3SiCl$ [M] | 4.4 wt. % | 4.3 wt. % |
| $CH_3HSiCl_2 + (CH_3)_2HSiCl$ | 2.1 wt. % | 0.9 wt. % |
| High Boilers | 2.1 wt. % | 1.7 wt. % |

The results in Table 3 show that a strong increase in reactivity and also an increase in selectivity were obtained when aluminium was added in the form of an AlCu alloy.

EXAMPLE 7

(Prior Art)

The reaction was repeated in the same manner as in Example 1, except that the reaction was catalysed with 8 grams of copper and promoted with zinc and antimony. The silicon used in this experiment was Silgrain® with a chemical composition of 0.22 wt. % Al, 0.22 wt. % Fe, 0.028 wt. % Ca, 0.012 wt. % Ti. The duration of the run was 288 minutes at when about 17% of the silicon was converted. The results are given in Table 4

EXAMPLE 8

(Present Invention)

The reaction was repeated in the same manner as in Example 7, except that 1 gram of an aluminium promoter consisting of gas atomised 70% Al30% Si alloy was added to the contact mass. The duration of the run was 302 minutes at when about 51% of the silicon was converted. The results are given in Table 4.

EXAMPLE 9

(Present Invention)

The reaction was repeated in the same manner as in Example 7, except that 0.7 gram of an aluminium promoter consisting of gas atomised Al was added to the contact mass. The duration of the run was 298 minutes at when about 50% of the silicon was converted. The results are given in Table 4.

TABLE 4

|  | Example 7 | Example 8 | Example 9 |
|---|---|---|---|
| Reactivity (gr. products/gr. Si * hr) | 0.18 | 0.67 | 0.66 |
| Selectivity [T/D] | 0.20 | 0.14 | 0.13 |
| $(CH_3)_2SiCl_2$ [D] | 75.3 wt. % | 79.6 wt. % | 80.9 wt. % |
| $CH_3SiCl_3$ [T] | 15.6 wt. % | 11.3 wt. % | 10.3 wt. % |
| $(CH_3)_3SiCl$ [M] | 5.5 wt. % | 5.3 wt. % | 4.6 wt. % |
| $CH_3HSiCl_2 + (CH_3)_2HSiCl$ | 1.4 wt. % | 2.4 wt. % | 2.2 wt. % |
| High Boilers | 2.2 wt. % | 1.4 wt. % | 2.0 wt. % |

The results in Table 4 show that a remarkable increase in reactivity and a pronounced increase in selectivity were obtained when aluminium was added in the form of metallic aluminium.

EXAMPLE 10

(Present Invention)

The reaction was repeated in the same manner as in Example 8, except that 0.25 gram of an aluminium promoter consisting of gas atomised 70% Al30% Si alloy was added to the contact mass. The duration of the run was 291 minutes at when about 35% of the silicon was converted. The results are given in Table 5.

EXAMPLE 11

(Present Invention)

The reaction was repeated in the same manner as in Example 8, except that 0.5 gram of an aluminium promoter consisting of gas atomised 70% Al30% Si alloy was added to the contact mass. The duration of the run was 315 minutes at when about 44% of the silicon was converted. The results are given in Table 5.

TABLE 5

|  | Example 7 | Example 10 | Example 11 | Example 8 |
|---|---|---|---|---|
| Reactivity (gr. products/ gr. Si * hr) | 0.18 | 0.42 | 0.51 | 0.67 |
| Selectivity [T/D] | 0.20 | 0.15 | 0.15 | 0.14 |
| $(CH_3)_2SiCl_2$ [D] | 75.3 wt. % | 81.4 wt. % | 78.8 wt. % | 79.6 wt. % |
| $CH_3SiCl_3$ [T] | 15.6 wt. % | 12.3 wt. % | 12.2 wt. % | 11.3 wt. % |
| $(CH_3)_3SiCl$ [M] | 5.5 wt. % | 3.7 wt. % | 5.4 wt. % | 5.3 wt. % |
| $CH_3HSiCl_2 + (CH_3)_2HSiCl$ | 1.4 wt. % | 1.7 wt. % | 2.0 wt. % | 2.4 wt. % |
| High Boilers | 2.2 wt. % | 0.9 wt. % | 1.6 wt. % | 1.4 wt. % |

The results in Table 5 show that an increasing amount of addition of the AlSi alloy gives a strong improvement in reactivity while the selectivity is improved by a small Al additive, but no further increase is observed when Al addition is increased.

EXAMPLE 12

(Prior Art)

The reaction was repeated in the same manner as in Example 3, except that the silicon used in this experiment was Sipearl® gas atomised silicon produced by Elkem a/s with a chemical composition of 0.15 wt. % Al, 0.45 wt. % Fe, 0.002 wt. % Ca, 0.018 wt. % Ti. The duration of the run was 421 minutes at when about 19% of the silicon was converted. The results are given in Table 6.

EXAMPLE 13

(Present Invention)

The reaction was repeated in the same manner as in Example 12, except that 1 gram of an aluminium promoter consisting of gas atomised 70% Al30% Si alloy was added to the contact mass. The duration of the run was 387 minutes at when about 25% of the silicon was converted. The results are given in Table 6.

TABLE 6

|  | Example 12 | Example 13 |
| --- | --- | --- |
| Reactivity (gr. products/gr. Si * hr) | 0.14 | 0.21 |
| Selectivity [T/D] | 0.05 | 0.06 |
| $(CH_3)_2SiCl_2$ [D] | 90.6 wt. % | 88.4 wt. % |
| $CH_3SiCl_3$ [T] | 4.4 wt. % | 5.1 wt. % |
| $(CH_3)_3SiCl$ [M] | 1.4 wt. % | 3.5 wt. % |
| $CH_3HSiCl_2 + (CH_3)_2HSiCl$ | 2.0 wt. % | 0.8 wt. % |
| High Boilers | 1.6 wt. % | 2.2 wt. % |

The results in Table 6 show that also when gas atomised silicon is used as silicon source in the reactor, a strong increase in reactivity is obtained by separately adding an AlSi alloy to the reactor, while the selectivity is still at an excellent level.

EXAMPLE 14

(Present Invention)

The reaction was repeated in the same manner as in Example 5, except that 7 grams of the Silgrain® was replaced with an aluminium containing silicon alloy having a chemical composition of 4.9 wt. % Al, 2.0 wt. % Fe, 0.05 wt. % Ca, 0.040 wt. % Ti. The duration of the run was 322 minutes at when about 18% of the silicon was converted. The results are given in Table 7.

EXAMPLE 15

(Present Invention)

The reaction was repeated in the same manner as in Example 5, except that 14 grams of the Silgrain® was replaced with an aluminium containing silicon alloy with a composition of 4.9 wt. % Al, 2.0 wt. % Fe, 0.05 wt. % Ca, 0.04 wt. % Ti. The duration of the run was 317 minutes at when about 20% of the silicon was converted. The results are given in Table 7.

TABLE 7

|  | Example 5 | Example 14 | Example 15 |
| --- | --- | --- | --- |
| Reactivity (gr. products/gr. Si * hr) | 0.11 | 0.17 | 0.19 |
| Selectivity [T/D] | 0.09 | 0.10 | 0.10 |
| $(CH_3)_2SiCl_2$ [D] | 83.8 wt. % | 82.4 wt. % | 83.6 wt. % |
| $CH_3SiCl_3$ [T] | 7.6 wt. % | 8.5 wt. % | 8.5 wt. % |
| $(CH_3)_3SiCl$ [M] | 4.4 wt. % | 5.5 wt. % | 5.2 wt. % |
| $CH_3HSiCl_2 + (CH_3)_2HSiCl$ | 2.1 wt. % | 2.5 wt. % | 1.7 wt. % |
| High Boilers | 2.1 wt. % | 1.2 wt. % | 1.1 wt. % |

The results in Table 7 show that a moderate increase in reactivity is obtained while maintaining a good selectivity by adding aluminium in the form of an aluminium containing silicon alloy containing 4.9% by weight of Al.

EXAMPLE 16

(Present Invention)

The reaction was repeated in the same manner as in Example 7, except that 3 grams of the Silgrain® silicon was replaced with an aluminium containing silicon alloy with a composition of 4.9 wt. % Al, 2.0 wt. % Fe, 0.05 wt. % Ca, 0.040 wt. % Ti. The duration of the run was 304 minutes at when about 30% of the silicon was converted. The results are given in Table 8.

EXAMPLE 17

(Present Invention)

The reaction was repeated in the same manner as in Example 7, except that 7 grams of the Silgrain® silicon was replaced with an aluminium containing silicon alloy with a composition of 4.9 wt. % Al, 2.0 wt. % Fe, 0.05 wt. % Ca, 0.04 wt. % Ti. The duration of the run was 299 minutes at when about 41% of the silicon was converted. The results are given in Table 8.

EXAMPLE 18

(Present Invention)

The reaction was repeated in the same manner as in Example 7, except that 14 grams of the Silgrain® silicon was replaced with an aluminium containing silicon alloy with a composition of 4.9 wt. % Al, 2.0 wt. % Fe, 0.05 wt. % Ca, 0.040 wt. % Ti. The duration of the run was 309 minutes at when about 43% of the silicon was converted. The results are given in Table 8.

TABLE 8

|  | Example 7 | Example 16 | Example 17 | Example 18 |
| --- | --- | --- | --- | --- |
| Reactivity (gr. products/ gr. Si * hr) | 0.18 | 0.32 | 0.50 | 0.52 |
| Selectivity [T/D] | 0.20 | 0.14 | 0.13 | 0.12 |
| $(CH_3)_2SiCl_2$ [D] | 75.3 wt. % | 79.5 wt. % | 81.4 wt. % | 83.4 wt. % |
| $CH_3SiCl_3$ [T] | 15.6 wt. % | 11.3 wt. % | 10.7 wt. % | 9.9 wt. % |
| $(CH_3)_3SiCl$ [M] | 5.5 wt. % | 4.9 wt. % | 4.5 wt. % | 4.1 wt. % |
| $CH_3HSiCl_2 + (CH_3)_2HSiCl$ | 1.4 wt. % | 3.2 wt. % | 1.8 wt. % | 1.8 wt. % |
| High Boilers | 2.2 wt. % | 1.1 wt. % | 1.5 wt. % | 0.9 wt. % |

The results in Table 8 show that both the reactivity and the selectivity were improved by adding aluminium in the form of an aluminium containing silicon alloy containing 4.9% by weight of Al and 2.0% by weight of Fe. The results further show that the improvement in reactivity increases with increasing addition of Si Al Fe alloy.

EXAMPLE 19

(Prior Art)

The reaction was repeated in the same manner as in Example 7, except that the silicon used in this experiment was a Silgrain® silicon with a chemical composition of 0.06 wt. % Al, 0.01 wt. % Fe, 0.008 wt. % Ca, 0.001 wt. % Ti. The duration of the run was 324 minutes at when about 5% of the silicon was converted. The results are given in Table 9

EXAMPLE 20

(Present Invention)

The reaction was repeated in the same manner as in Example 19, except that 14 grams of the Silgrain® silicon was replaced with an aluminium containing silicon alloy with a composition of 4.9 wt. % Al, 2.0 wt. % Fe, 0.05 wt. % Ca, 0.040 wt. % Ti. The duration of the run was 382 minutes at when about 51% of the silicon was converted. The results are given in Table 9.

TABLE 9

|  | Example 19 | Example 20 |
| --- | --- | --- |
| Reactivity (gr. products/gr. Si * hr) | 0.04 | 0.53 |
| Selectivity [T/D] | 0.30 | 0.11 |
| $(CH_3)_2SiCl_2$ [D] | 69.3 wt. % | 83.4 wt. % |
| $CH_3SiCl_3$ [T] | 20.5 wt. % | 19.1 wt. % |
| $(CH_3)_3SiCl$ [M] | 1.4 wt. % | 4.8 wt. % |
| $CH_3HSiCl_2 + (CH_3)_2HSiCl$ | 6.0 wt. % | 1.1 wt. % |
| High Boilers | 2.7 wt. % | 1.5 wt. % |

The results in Table 9 show that by separate addition of aluminium it is possible to obtain a high reactivity and good selectivity for a silicon which normally is considered to be very low reactive in the direct process.

EXAMPLE 21

(Prior Art)

The reaction was repeated in the same manner as in Example 1, except that the silicon used in this experiment was of metallurgical grade with a chemical composition of 0.10 wt. % Al, 0.28 wt. % Fe, 0.029 wt. % Ca, 0.021 wt. % Ti. The silicon was sized in a disk pulveriser and screened to a particle size of 71–250 µm. The duration of the run was 330 minutes at when about 8% of the silicon was converted. The results are given in Table 10.

EXAMPLE 22

(Present Invention)

The reaction was repeated in the same manner as in Example 21, except that 7 grams of the silicon was replaced with an aluminium containing silicon alloy with a composition of 4.9 wt. % Al, 2.0 wt. % Fe, 0.05 wt. % Ca, 0.040 wt. % Ti. The duration of the run was 284 minutes at when about 19% of the silicon was converted. The results are given in Table 10.

TABLE 10

|  | Example 21 | Example 22 |
| --- | --- | --- |
| Reactivity (gr. products/gr. Si * hr) | 0.07 | 0.20 |
| Selectivity [T/D] | 0.30 | 0.20 |
| $(CH_3)_2SiCl_2$ [D] | 63.3 wt. % | 72.1 wt. % |
| $CH_3SiCl_3$ [T] | 19.2 wt. % | 14.6 wt. % |
| $(CH_3)_3SiCl$ [M] | 10.0 wt. % | 9.1 wt. % |
| $CH_3HSiCl_2 + (CH_3)_2HSiCl$ | 6.0 wt. % | 2.8 wt. % |
| High Boilers | 1.4 wt. % | 1.4 wt. % |

The results in Table 10 show that also for this kind of low reactive silicon, separate addition of aluminium gives an increase both in reactivity and selectivity.

EXAMPLE 23

(Prior Art)

The reaction was repeated in the same manner as in Example 7, except that the silicon used in this experiment was of metallurgical grade with a chemical composition of 0.11 wt. % Al, 0.22 wt. % Fe, 0.005 wt. % Ca, 0.017 wt. % Ti. The silicon was sized in a disk pulveriser and screened to a particle size of 71–250 µm. The duration of the run was 349 minutes at when about 22% of the silicon was converted. The results are given in Table 11.

EXAMPLE 24

(Present Invention)

The reaction was repeated in the same manner as in Example 23, except that 7 grams of the silicon was replaced with an aluminium containing silicon alloy with a composition of 4.9 wt. % Al, 2.0 wt. % Fe, 0.05 wt. % Ca, 0.040 wt. % Ti. The duration of the run was 189 minutes at when about 25% of the silicon was converted. The results are given in Table 11.

EXAMPLE 25

(Present Invention)

The reaction was repeated in the same manner as in Example 23, except that 0.7 gram of an aluminium promoter consisting of gas atomised Al was added to the contact mass. The duration of the run was 304 minutes at when about 48% of the silicon was converted. The results are given in Table 11.

TABLE 11

|  | Example 23 | Example 24 | Example 25 |
| --- | --- | --- | --- |
| Reactivity (gr. products/gr. Si * hr) | 0.20 | 0.43 | 0.60 |
| Selectivity [T/D] | 0.16 | 0.15 | 0.15 |
| $(CH_3)_2SiCl_2$ [D] | 76.3 wt. % | 79.7 wt. % | 78.6 wt. % |
| $CH_3SiCl_3$ [T] | 12.4 wt. % | 11.7 wt. % | 11.9 wt. % |
| $(CH_3)_3SiCl$ [M] | 5.2 wt. % | 5.3 wt. % | 5.4 wt. % |
| $CH_3HSiCl_2 + (CH_3)_2HSiCl$ | 3.6 wt. % | 1.9 wt. % | 2.8 wt. % |
| High Boilers | 2.5 wt. % | 1.4 wt. % | 1.3 wt. % |

The results in Table 11 show that good results are obtained both by addition of SiAlFe alloy and by addition of metallic aluminium.

I claim:

1. In a method for production of alkylhalosilanes by reaction between elemental silicon and an alkylhalide at elevated temperatures in the presence of a copper-based catalyst, the improvement comprising adding a separate aluminium promoter in the form of a solid metallic aluminium, or a solid aluminium alloy, or a solid aluminium containing silicon alloy or a solid aluminium containing compound or mixtures thereof to the reactor at the start of the reaction in an amount between 0.01 and 1% by weight calculated as aluminium based on the weight of silicon supplied to the reactor, said aluminium promoter being added as a separate component from said silicon, said alkylhalide, and said copper-based catalyst; and maintaining the amount of aluminium promoter in the reactor during the reaction at between 0.01 and 1% by weight silicon in the reactor.

2. The method according to claim 1, characterized in that the metallic aluminium, the aluminium alloy, the aluminium containing silicon alloy, the solid aluminium containing compound and mixtures thereof are added in the form of a mechanical mixture with the silicon and/or the catalyst.

3. The method according to claim 1, characterized in that the metallic aluminium, the aluminium alloy, the aluminium containing silicon alloy, the solid aluminium containing compound or mixtures thereof are added to the reactor separately from the silicon and the catalyst.

4. The method according to claim 1, characterized in that the metallic aluminium or the aluminium alloy or the aluminium containing silicon alloy or the solid aluminium containing compound or mixtures thereof are added to the reactor in an mount between 0.05 and 0.20% by weight calculated as aluminium based on the weight of silicon supplied to the reactor.

5. The method according to claim 1, characterized in that the aluminium promoter is added in the form of aluminium alloys containing one or more of the elements Si, Cu, Fe, Mg, Zn and Ca.

6. The method according to claim 1, characterized in that the aluminium promoter is added in the form of an aluminium containing silicon alloy containing at least 0.5% by weight of Al.

7. The method according to claim 6, characterized in that the aluminium promoter is added in the form of an aluminium containing silicon alloy which also contains Fe and/or Cu.

8. The method according to claim 1, characterized in that the addition of aluminium promoter is adjusted in order to keep a preset ratio of aluminium to silicon in the reactor.

* * * * *